United States Patent
Knutsson

(10) Patent No.: US 9,844,646 B2
(45) Date of Patent: Dec. 19, 2017

(54) NEEDLE TIP SHIELDING DEVICE AND FIXING ARRANGEMENT

(71) Applicant: Vigmed AB, Helsingborg (SE)

(72) Inventor: Per Knutsson, Helsingborg (SE)

(73) Assignee: VIGMED AB (SE)

( * ) Notice: Subject to any disclaimer, the term of this patent is extended or adjusted under 35 U.S.C. 154(b) by 15 days.

(21) Appl. No.: 14/407,810

(22) PCT Filed: Jun. 7, 2013

(86) PCT No.: PCT/SE2013/050651
§ 371 (c)(1),
(2) Date: Dec. 12, 2014

(87) PCT Pub. No.: WO2013/187827
PCT Pub. Date: Dec. 19, 2013

(65) Prior Publication Data
US 2015/0126932 A1 May 7, 2015

(30) Foreign Application Priority Data
Jun. 15, 2012 (SE) ........................ 1250635

(51) Int. Cl.
*A61M 25/06* (2006.01)
(52) U.S. Cl.
CPC .... *A61M 25/0618* (2013.01); *A61M 25/0606* (2013.01); *A61M 25/0625* (2013.01)
(58) Field of Classification Search
CPC .......... A61M 25/0618; A61M 25/0612; A61M 25/0097; A61M 25/0102; A61M 25/0606; A61M 25/0625
See application file for complete search history.

(56) References Cited

U.S. PATENT DOCUMENTS

| | | | |
|---|---|---|---|
| 5,697,914 A * | 12/1997 | Brimhall ........... | A61M 25/0637 604/164.01 |
| 6,379,333 B1 * | 4/2002 | Brimhall ............. | A61M 5/3273 604/110 |
| 7,670,317 B2 * | 3/2010 | Cindrich ............... | A61M 5/158 604/167.01 |

(Continued)

FOREIGN PATENT DOCUMENTS

| | | | | |
|---|---|---|---|---|
| AU | 2006203663 A1 * | 2/2008 | ........ | A61M 25/0618 |
| CN | 101112639 A | 1/2008 | | |

(Continued)

OTHER PUBLICATIONS

English Translation of CN 101112639A. Otained from Global Patent Search Network on Dec. 2, 2016.*

(Continued)

*Primary Examiner* — Kami A Bosworth
(74) *Attorney, Agent, or Firm* — Fishman Stewart PLLC

(57) ABSTRACT

A closed IV catheter system, includes a needle shield assembly positioned proximally of a catheter hub and distally of the needle hub. The needle shield assembly cooperates with the catheter hub on the outer circumferential and peripheral surface of the catheter hub. The needle shield adds additional length and width to the closed IV catheter system. An improved manufacturing process with unique materials is also presented.

20 Claims, 3 Drawing Sheets

(56) References Cited

U.S. PATENT DOCUMENTS

| | | | |
|---|---|---|---|
| 7,798,994 B2* | 9/2010 | Brimhall | A61M 25/0618 604/110 |
| 2003/0060771 A1* | 3/2003 | Bialecki | A61M 25/0618 604/164.08 |
| 2005/0277879 A1* | 12/2005 | Daga | A61M 25/0618 604/110 |
| 2006/0155245 A1* | 7/2006 | Woehr | A61M 25/0618 604/164.08 |
| 2007/0112305 A1 | 5/2007 | Brimhall | |
| 2008/0097344 A1* | 4/2008 | McKinnon | A61M 25/0637 604/263 |
| 2009/0312711 A1* | 12/2009 | Brimhall | A61M 25/0618 604/164.08 |
| 2010/0168675 A1 | 7/2010 | Cindrich et al. | |
| 2012/0035552 A1* | 2/2012 | Woehr | A61M 5/3273 604/246 |

FOREIGN PATENT DOCUMENTS

| | | |
|---|---|---|
| EP | 0268480 A1 | 5/1988 |
| EP | 0497576 A1 | 8/1992 |
| WO | WO-9908742 A1 | 2/1999 |
| WO | WO-2004004819 A1 | 1/2004 |
| WO | WO-2004032995 A2 | 4/2004 |
| WO | WO-2004087247 A2 | 10/2004 |
| WO | WO-2007050788 A2 | 5/2007 |
| WO | WO-2008052791 A1 | 5/2008 |
| WO | WO-2012016660 A1 | 2/2012 |
| WO | WO-2012039672 A1 | 3/2012 |
| WO | WO-2013187827 A1 | 12/2013 |

OTHER PUBLICATIONS

English Abstract of CN 101112639 (A) (Date of CN 101112639 (A) : Jan. 30, 2008).

* cited by examiner

NEEDLE TIP SHIELDING DEVICE AND FIXING ARRANGEMENT

CROSS-REFERENCE TO RELATED APPLICATIONS

This application is a U.S. National phase based on PCT/SE2013/050651, filed on Jun. 7, 2013 entitled "NEEDLE TIP SHIELDING DEVICE AND FIXING ARRANGEMENT" which is based on Swedish Patent Application No. 1250635-8, filed on Jun. 15, 2012.

TECHNICAL FIELD

The present disclosure pertains to a closed IV catheter system, comprising a needle hub, a catheter hub with a catheter connected distally of an adapter body, said adapter body having an extension tube extending laterally from the adapter body, wherein the extension tube is in fluid communication with an inner adapter body cavity and the lumen of the catheter, and a needle shield assembly.

BACKGROUND

Catheters, particularly intravascular (IV) catheters, are used for infusing fluid, such as normal saline solution, various medicaments and total parenteral nutrition, into a patient, withdrawing blood from a patient or monitoring various parameters of the patient's vascular system. Peripheral IV catheters tend to be relatively short, and typically are on the order of about two inches or less in length.

The most common type of IV catheter is an over-the-needle peripheral IV catheter.

As its name implies, an over-the-needle catheter is mounted over an introducer needle having a sharp distal tip. At least the distal portion of the catheter tightly engages the outer surface of the needle to prevent peelback of the catheter and thus facilitates insertion of the catheter into the blood vessel. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

With regard to over-the-needle catheters, there are mainly two major alternatives. The first one, the open IV catheter system, such as the Venflon®-type, comprises luer through which the needle is withdrawn after insertion of the catheter into the blood vessel, which is connectable to blood withdrawal or infusion means, as well as an optional port for the same purpose. The second one, the closed IV catheter system, such as the Nexiva™-type, comprises a septum in an catheter hub through which the needle is withdrawn after insertion of the catheter into the blood vessel, closing off the "needle channel" from the environment, and instead has an extension tube extending laterally from the catheter hub, wherein the extension tube is in fluid communication with the catheter hub cavity and the lumen of the catheter positioned in the blood vessel. These two alternatives are accompanied with different problems and benefits.

In recent years, there has been great concern over the contamination of clinicians with a patient's blood and a recognition that "blood contaminated sharps" must be disposed to avoid an accidental needle stick. This concern has arisen because of the advent of currently incurable and fatal diseases, such as Acquired Immunosuppressive Deficiency Syndrome ("AIDS"), hepatitis, etc., which can be transmitted by the exchange of body fluids from an infected person to another person.

As a result of the problem of accidental needlesticks by "blood contaminated sharps", various needle shields have been developed for use in conjunction with intravenous catheters. Due to the difference in configuration between an open and a closed IV catheter system, different needle shields and configurations have been introduced with regard to the two alternatives.

With regard to closed IV catheter systems, the catheter hub has to be of a material compatible with adhesion of the extension tubing. Such a material is for example polycarbonate, which is a hard and brittle polymer with a high impact strength. Additionally, the septum in the catheter hub takes up the proximal part of the catheter hub.

The present disclosure discloses a closed IV catheter system, wherein a needle shield assembly is positioned proximally of the catheter hub and distally of the needle hub, and wherein the needle shield assembly cooperates with the catheter hub on the outer circumferential and peripheral surface of the catheter hub. This means that the needle shield adds additional length and width to the closed IV catheter system. Additionally, the needle shield assembly could be reached and perhaps released unintentionally from the catheter hub, and not as envisioned only by withdrawal of the needle hub.

Hence, a needle shield assembly with improved volume occupying characteristics, as well as decreased risk of undue needle shield assembly release with regard to a closed IV catheter system, is desired.

SUMMARY

It is an aspect of the present disclosure, considering the disadvantages mentioned above, to provide a closed IV catheter system with a needle shield, while avoiding unnecessarily adding to dimensions thereof.

It is another aspect of the present disclosure, to provide an IV catheter system which may be produced at low cost.

These and other aspects, which will appear from the following description, have now been achieved by an exemplary IV catheter system comprising: a catheter hub, said catheter hub comprising: a tubular catheter attached to a catheter hub body at its proximal end; a catheter hub cavity in fluid communication with the lumen of the tubular catheter; a tube in fluid communication with the catheter hub cavity, said tube extending laterally from the catheter hub body; a septum, proximally of the catheter hub cavity; and an end cavity, proximally of the septum; a needle hub, said needle hub comprising: a needle extending distally from a needle hub body, said needle having a bulge at its distal end zone; a needle shield, said needle shield comprising: at least one resilient arm extending distally from a base plate, said base plate having a through hole for receiving the needle there through; wherein the needle hub is arranged in the catheter hub, such that the needle is slidingly arranged through said septum and in the lumen of said catheter, such that the needle may be withdrawn proximally from the catheter hub; wherein the needle shield is arranged in the end cavity in a retained manner through cooperation between the needle shield and an inner wall of the catheter hub in said end cavity, and onto the needle, such that the at least one arm rests upon and is spring loaded by the needle, and the needle is slidingly arranged within the through hole of the base plate, in an assembled state; and wherein the bulge will interact with the base plate when the needle hub is withdrawn from the catheter hub to release the needle shield from the catheter hub and the at least one arm will cover the tip of the needle, in a released state.

Further features of the disclosure and its embodiments are set forth in the appended claims.

BRIEF DESCRIPTION OF THE DRAWINGS

These and other aspects, features and advantages of which the disclosure is capable will be apparent and elucidated from the following description of non-limiting embodiments of the present disclosure, reference being made to the accompanying drawings, in which.

DETAILED DESCRIPTION OF THE EMBODIMENTS

Embodiments of the present disclosure will be described in more detail below with reference to the accompanying drawings in order for those skilled in the art to be able to carry out the disclosure. The disclosure may, however, be embodied in many different forms and should not be construed as limited to the embodiments set forth herein. Rather, these embodiments are provided so that this disclosure will be thorough and complete, and will fully convey the scope of the disclosure to those skilled in the art.

Furthermore, the terminology used in the detailed description of the particular embodiments illustrated in the accompanying drawings is not intended to be limiting of the disclosure. More specifically, the term "proximal" refers to a location or direction of items or parts of items, during normal use of the closed IV catheter system disclosed herein, is closest to the user, i.e. the clinician, and farthest away from the patient receiving the closed IV catheter system. Similarly, the term "distal" refers to a location or direction of items or parts of items, during normal use of the closed IV catheter system disclosed herein, is closest to the patient and farthest away from the clinician. The term "laterally" refers to the direction away from the central axis of the closed IV catheter system, such that at least a vector component perpendicular to the central axis of the closed IV catheter system, wherein the needle and catheter of the assembled closed IV catheter system coincides with the central axis of the closed IV catheter system.

Figure 1:
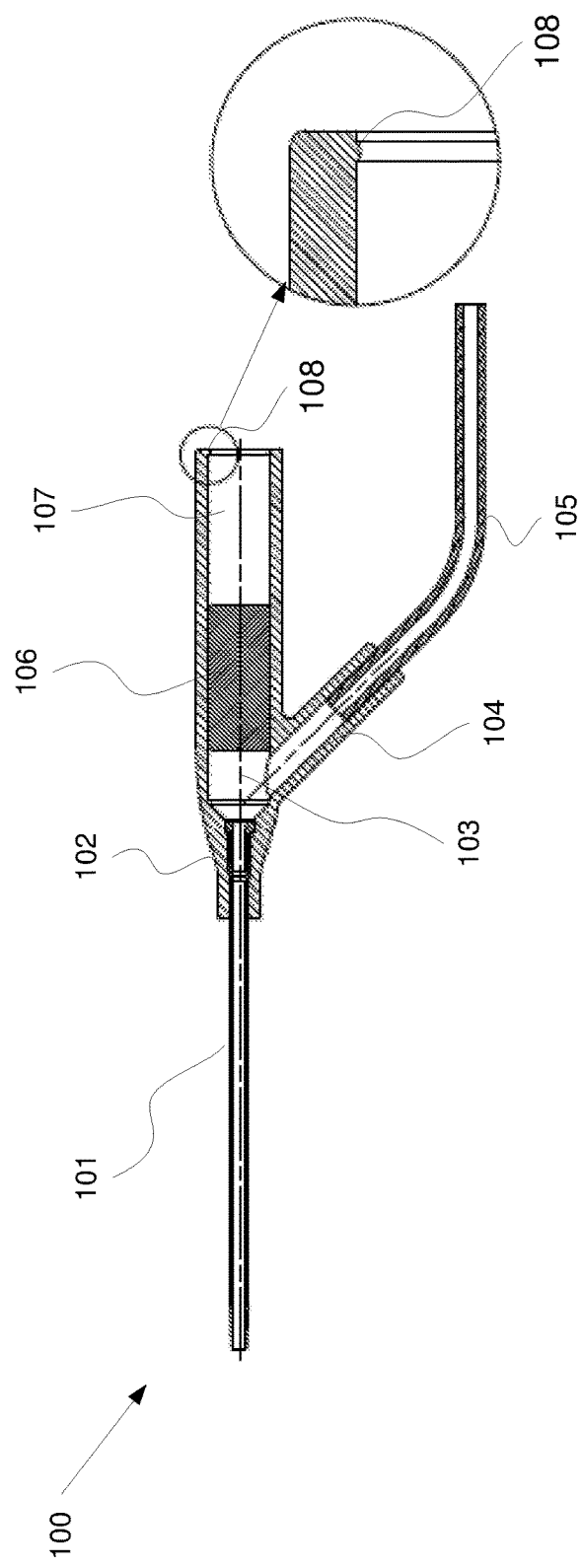
FIG. 1 is a cross-sectional view of a catheter hub according to one embodiment of the present disclosure.

In accordance with FIG. 1, one embodiment of a catheter hub 100 of a closed IV catheter system is illustrated. The catheter hub 100 comprises a longitudinal and tubular catheter 101 at its distal end. The catheter is, in accordance with above, intended to be inserted into a blood vessel of a patient. The catheter 101 is attached to a catheter hub body 102 at its proximal end, such that the catheter extends distally from the catheter hub body 102. The lumen of the catheter 101 is in fluid communication with a catheter hub cavity 103. The catheter hub body 102 is preferably made through injection molding, and then of a rigid plastic material suitable for injection molding and connection and interaction with other parts of the system. Such a suitable material is polycarbonate or a copolymer of polycarbonate and polyester.

From the catheter hub body 102 a tube connector 104 is provided. The tube connector 104 extends laterally from the catheter hub body 102. The tube connector 104 has a lumen in fluid communication with the hub cavity 103, such that a tube 105 may be connected to the tube connector 104 to allow for infusion from the tube 105 into the tube connector 104, further into hub cavity 103 to catheter 101, and finally into the blood stream of the patient. The tube connector 104 may for example be tubular. A suitable material for the tube 105 is polyvinyl chloride or ethylene vinyl acetate.

Figure 2A:
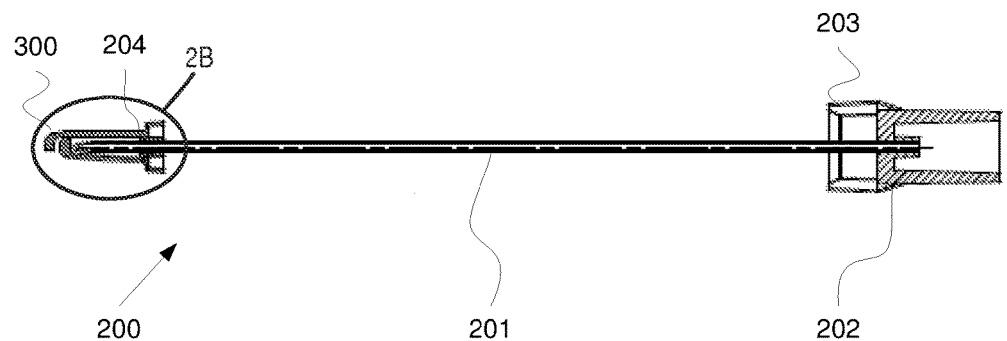
FIG. 2A is a cross-sectional view of a needle hub, with a needle shield arranged thereon, according to one embodiment of the present disclosure.
Figure 2B:
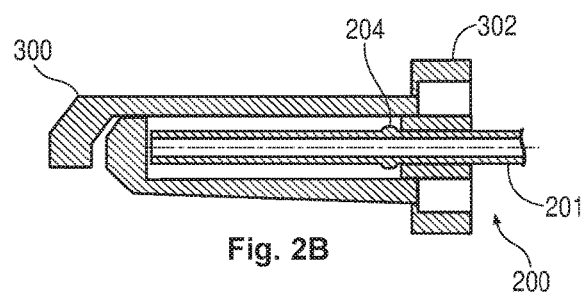
FIG. 2B is an enlarged cross-sectional view of FIG. 2A.

The catheter hub cavity 103 ends proximally in a septum 106. This septum 106 has a central through channel, which may be penetrated by a needle 201 of a needle hub 200, in accordance with FIG. 2A. When the needle 201 has been withdrawn from the catheter hub 100, the septum 106 will close said through channel, such that the hub cavity 103 is marked off from the surroundings in the proximal direction. For this reason, the septum 106 is preferably of a suitable rubber material or silicone.

Figure 3:
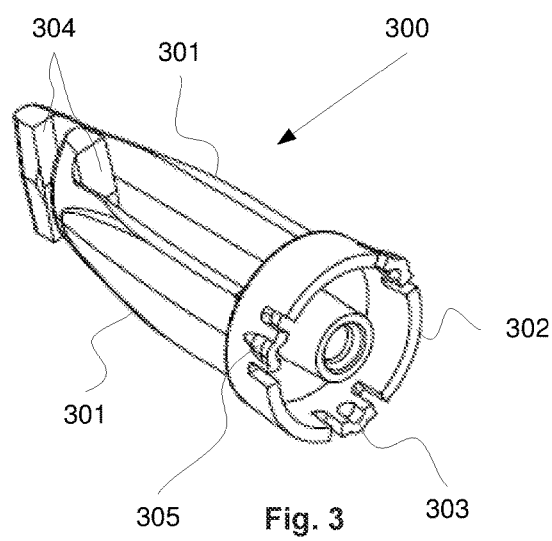
FIG. 3 is a perspective view of a needle shield according to one embodiment of the present disclosure, intended to be arranged on a needle of a needle hub according to FIG. 2A which in turn is intended to be arranged in the catheter hub according to FIG. 1.

On the proximal side of the septum 106 a proximal end cavity 107 is located. The end cavity 107 is formed by the tubular wall of the catheter hub body 102 and a distal end wall in form of the proximal end wall of the septum 106. This end cavity 107, extending distally into the catheter hub body 102, is adapted in size and shape to house the needle shield 300, as disclosed in FIG. 3.

Figure 4:
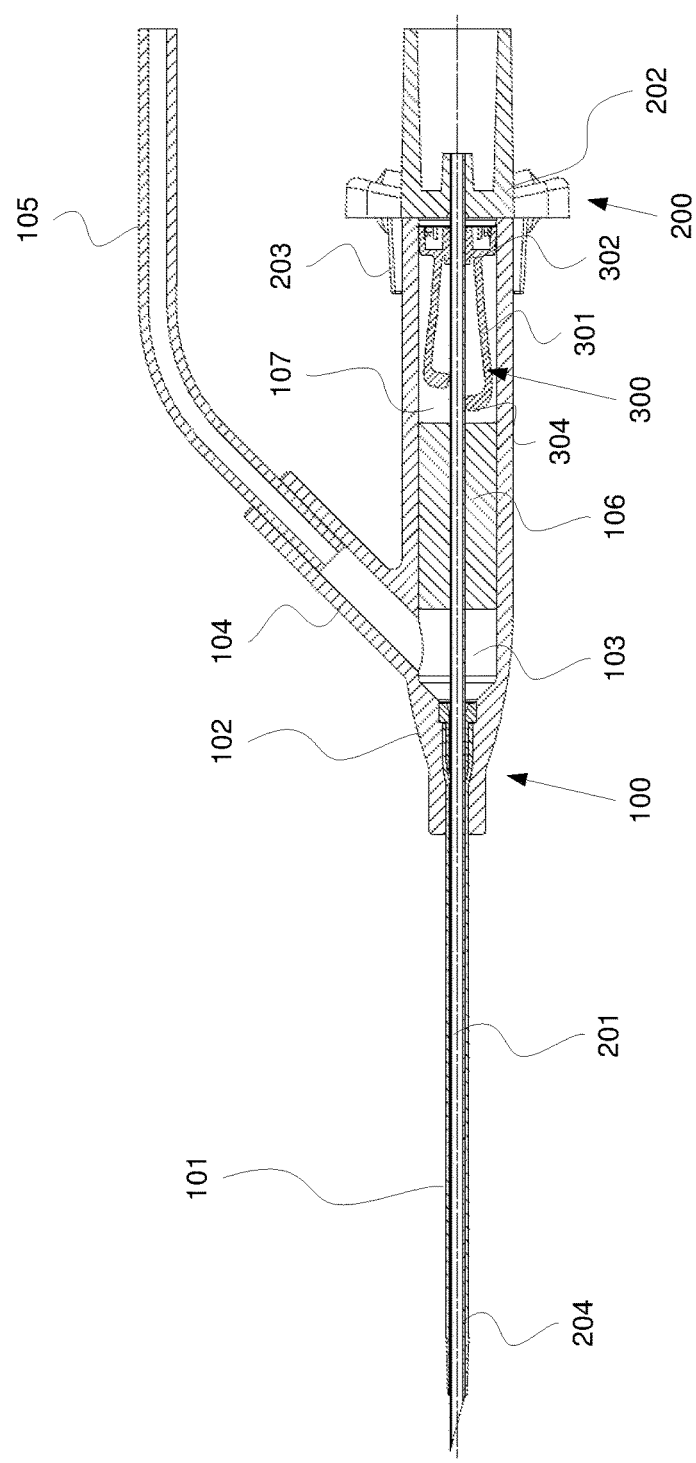
FIG. 4 is a cross-sectional view of a closed IV catheter system, with a catheter hub, a needle hub, and a needle shield, in assembled state, in accordance with an embodiment of the present disclosure.

The needle shield 300 is thus intended to be arranged on the needle 201 of the needle hub 200, which in turn is intended to be arranged in the catheter hub 100. In such assembled state, in accordance with FIG. 4, the needle 201 penetrates the septum 106, and extends through the catheter 101. Preferably, the needle 201 extends just beyond the distal end of the catheter 101, such that skin and blood vessel penetration is facilitated. In that position, the needle shield 300 is arranged in the end cavity 107, with arms 301 thereof forced laterally by needle 201. The needle shield 300 preferably does not extend proximally of the proximal end of the catheter hub 100, but is instead entirely housed in the end cavity 107 of the catheter hub 100. In this way, the needle hub body 202 of the needle hub 200 may cooperate with the catheter hub body 102 of the catheter hub 100, without intermediary structures, such as the needle shield 300. This may be accomplished through a distal connective flange 203 on the needle hub 200. The distal connective flange 203 may then house the distal end of the catheter body 102 of the catheter hub 100. This connection may be a snap fit. Alternatively, the needle hub body 202 has a distal cavity for housing a part of the needle shield 300, while still being adapted to be connectable to the catheter hub body 102. In this position the needle shield 300 is held in place in the proximal end cavity 107 through interaction between a needle shield base plate 302 and the inner tubular wall of the catheter hub body 102. This may be accomplished by tongues 303, extending laterally of the base plate 302, being flexed somewhat inwardly to exercise a lateral pressure on the inner tubular wall of the catheter hub body 102 inside the end cavity 107. To further increase the cooperation between the periphery of the needle shield 300 and the catheter hub 100 a circumferential ridge 108 may be formed at the opening of the end cavity 107. The base plate 302 is provided with a centrally arranged through hole, such that the needle 200 may run freely therein.

When withdrawing the needle hub 200 from the catheter hub 100, after the catheter 101 has been securely placed inside the blood vessel of the patient, the needle hub 200 will firstly be disconnected from the cooperation between the catheter hub body 102 and the needle hub body 202, such as through release of the connective flange 203 from the circumference of the catheter body 102. Then the needle 201 travels proximally within the catheter 101, until the needle tip of the needle 201 exits the catheter 101 and enters the catheter hub body 102. When entering the catheter hub body 102, the needle tip of the needle 201 will continue proximally into the catheter hub cavity 103 and further through the septum 106. While the needle tip of the needle 201 travels proximally through the septum 106, the septum 106 will continuously seal off the catheter hub cavity 103 from the surroundings in the proximal direction. When the needle tip of the needle 201 exits the septum on the proximal side thereof, the needle tip of the needle 201 enters the proximal end cavity 107 of the catheter hub 100, wherein the needle shield 300 is positioned and is securingly interacting with the inner tubular wall of the catheter hub body 102. When the needle tip of the needle 201 passes proximally of the arms 301, the arms 301 will snap centrally to cover the needle tip of the needle 200. This may be further facilitated by hooked tips 304 on the arms 301. Just subsequently to the snapping of the arms 301 in front of the tip of the needle 201, a bulge 204 on the needle 201 hits the base plate 302. The bulge 204 has a width that is greater than the central lumen of the base plate 302. Thus, the withdrawal of the needle hub 200 further proximally will pull out the needle shield 300 from the end cavity 107. This is accomplished by adapting the retaining action from tongues 303, such that the retaining force from these is overcome by a suitable withdrawal force. Then the needle hub is separated from the catheter hub, and the needle shield 300 is securely arranged on the tip of the needle 200 to prohibit and prevent accidental needle stick.

The needle shield 300 may comprise one, two, three or more tongues 303, which extend proximally from the lateral circular periphery of the base plate 302. The tongues 303 are, in accordance with above, resilient, whereby they are resiliently striving from a compressed state towards an expanded state. In the assembled state within the end cavity 107, the tongues 303 are somewhat compressed, to exercise a force on the inner walls of the catheter hub 100. The needle shield 300 is thereby held therein, i.e. a constant spatial relationship between the needle shield 300 and the catheter hub 100 is provided. A plurality of tongues 303 may be evenly spread at the periphery of the base plate 302, whereby each tongue 303 is contacting the inner surface of the catheter hub 100 with essentially the same force.

The tongues 303 may comprise a protuberance 305 extending in a direction essentially perpendicular to the central axis or laterally of the needle shield 300. When the tongues 303 are provided with protuberances 305, the diameter of the base plate 302 in a transversal plane intersecting the protuberances 305 may be greater than the diameter of the end cavity 107, and specifically the proximal opening thereof, along a transversal plane. Then the needle shield 300 may be compressed, due to the flexibility of the tongues 303, such that it may be inserted into the end cavity 107 in a compressed state. In the inserted position, the protuberances 305 on the tongues 303 then exerts a retaining radially outwards directed pressure on the inner wall of the end cavity 107. The ridge 108 of at the opening of the end cavity 107 then maintains the needle shield 300 within the cavity, until the needle 201 pulls the needle shield proximally, whereby the pressure of the protuberances 305 on the inner walls of the end cavity 107 is overcome and the also the protuberances 305 are pressed inwardly beyond the ridge 108 to release the needle shield 300 from the end cavity 107. To facilitate interaction between the needle shield 300 and the end cavity 107, the ridge 108 is somewhat slanting distally and/or proximally. The protuberances 305 are in the same way slanting distally and/or proximally. Preferably the slanting of the protuberances is sharper in the proximal direction than in the distal direction, whereby the needle shield 300 may be smoothly inserted into the end cavity 107, retained with a snap action when the proximal side of the protuberances pass distally beyond the ridge 108, and also maintained more securely due to the sharper slanting at the proximal zone.

According to one embodiment, the needle shield 300 may be made of a plastic material. Preferably, the plastic material has a suitable combination, for its intended purpose, of tenacity, rigidity, fatigue resistance, elasticity, and creep deformation resistance. A suitable plastic material has a high creep deformation resistance, i.e. it has a low tendency to slowly move or deform permanently under the influence of an applied external pressure. Hence, a catheter system of the present disclosure, comprising needle shield 300, may be stored in the assembled ready mode for a prolonged time without extensive creep deformation of the arms 301 or the tongues 303. Advantages of a plastic needle shield 300 include the highly reduced tendency, in comparison to metal, of release of e.g. microscopic plastic chips by the scraping of the plastic catheter hub 100, when the needle shield 300, is ejected from the former upon withdrawal of the needle 201. Accordingly, the tendency for formation of scrape marks, which may result in leakage through the affected connector, is greatly reduced. In addition, a plastic needle tip shielding device may be easily color coded or transparent, depending on its particular application.

The needle shield 300 is a monolithic or homogenous injection molded needle shielding 300, made of a molded plastic material. Due to the specific configuration of the different parts of the needle shield 300 according to the embodiments of the present disclosure, the needle shield 300 may be molded, such as injection molded, into one homogenous, i.e. monolithic, piece and/or one integral unit, without interfaces in between the different parts thereof. Advantages of a monolithic needle shield 300 include a lower production cost in comparison to other devices made of more than one part that has to be assembled. The needle shield 300 may in this respect be made of a thermoplastic polymer. The thermoplastic polymer could be crystalline, amorphous, or comprising crystalline and amorphous alternating regions. A creep resistance of the thermoplastic polymer of choice may preferably be at least 1200 MPa (ISO 527, ASTM D638). Suitable plastics for the needle shield 300 may be selected from the group comprising of polyoxymethylene (POM), polybutylen terephthalate (PBTP), polymethyl methacrylate (PMMA), acrylonitrile butadiene styrene (ABS), styrene acrylonitrile (SAN), acrylonitrile styrene acrylate (ASA), polystyrene (PS), styrene butadiene (SB), liquid crystal polymer (LCP), polyamide (PA), polysulfone (PSU), polyetherimide (PEI), polycarbonate (PC), polyphenylene oxide (PPO), and/or PPO/SB, and co- and terpolymers thereof. These polymers have specifically the advantages of providing enhanced storing capacity, even in strained state, and excellent cooperation abilities with regard to the catheter hub, due to the excellent structure memory of these polymers.

Contacting smooth shapes of two bodies, such as a needle shield 300 mounted in a catheter hub 100, may result in a significant attraction between these bodies, especially if the contact area is large and they are pressed together. The underlying basis for this type of attraction include intermolecular attraction between the molecules of the two bodies, in which molecular van der Waals interactions and surface tension of the two bodies are important factors. Covalent bond formation between closely interacting surfaces may also contribute to the attraction. Such covalent bond formation, and other types of attraction between two surfaces, may also result upon radiation treatment, such as radiation treatment of e.g. catheter instrument to sterilize these. This type of attraction may become noticeable when the needle shield 300 is about to be released from the catheter hub 100. The force needed to release the needle shield 300 from the catheter hub 100 then becomes significantly higher than expected. This effect, which may be referred to as "the attraction effect", may even adventure the intended function of the needle tip shielding device if relying on e.g. an automatic release of a part of the device, such as a spring biased arm or the like, from a part of the catheter hub. The needle shield 300 is kept in contact with the catheter hub 100 in the assembled state via at least one interface surface between the needle shield 300 and the catheter hub 100. Thus, in one embodiment the surface of the needle shield 300 being in contact with the inner lumen of the catheter hub is of a different polymeric material than the polymeric material of the catheter hub.

At the other end of the tube 105 a unit with branches (not shown) may be attached to the tube 105. The branches may in turn be provided with standard Luer Slip® or Luer Lok® connections and corresponding lids, for allowing infusion into the tube 105.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. An IV catheter system comprising:
a catheter hub, said catheter hub comprising:
a tubular catheter attached at a proximal end to a catheter hub body;
a catheter hub cavity in fluid communication with a lumen of the tubular catheter;
a tube in fluid communication with the catheter hub cavity, said tube extending laterally from the catheter hub body;
a septum, proximal of the catheter hub cavity; and
an end cavity, proximal of the septum;
a needle hub, said needle hub comprising:
a needle extending distally from a needle hub body, a distal end zone of said needle having a bulge; and
a needle shield, said needle shield comprising:
at least one resilient arm extending distally from a base plate, said base plate having a through hole for receiving the needle therethrough;
wherein the needle hub is arranged in the catheter hub, such that the needle is slidingly arranged through said septum and in the lumen of said catheter, such that the needle may be withdrawn proximally from the catheter hub;
wherein the needle shield is arranged to be entirely housed in the end cavity in a retained manner through direct interaction between the needle shield and an inner wall of the catheter hub body in said end cavity, and onto the needle, such that the at least one arm rests upon and is spring loaded by the needle, and the needle is slidingly arranged within the through hole of the base plate, in an assembled state; and
wherein the bulge interacts with the base plate when the needle hub is withdrawn from the catheter hub to release the needle shield from the catheter hub and with the at least one arm covering a tip of the needle while the septum provides a seal, thereby forming a closed system in a released state.

2. The IV catheter system according to claim 1, wherein the catheter hub comprises a tube connector extending laterally from the catheter hub body, and the tube in turn is attached to the tube connector.

3. The IV catheter system according to claim 1, wherein a proximal end of the end cavity is provided with a ridge.

4. The IV catheter system according to claim 1, wherein the catheter hub body is manufactured in polycarbonate or a copolymer of polycarbonate and polyester.

5. The IV catheter system according to claim 1, wherein the catheter hub body is injection molded.

6. The IV catheter system according to claim 1, wherein the septum is made of silicone or rubber.

7. The IV catheter system according to claim 1, wherein the tube is made of polyvinyl chloride or ethylene vinyl acetate.

8. The IV catheter system according to claim 1, wherein a proximal end of the catheter hub body cooperates with a distal end of the needle hub body in the assembled state.

9. The IV catheter system according to claim 1, wherein a distal connective flange of the needle hub body cooperates with an outer proximal surface of the catheter hub body in a retaining manner.

10. The IV catheter system according to claim 1, wherein the needle shield cooperates with the inner wall of the catheter hub body in the end cavity through a periphery of the base plate, and
wherein the at least one arm snaps centrally to cover the needle tip in response to the needle tip passing proximally of the at least one arm.

11. The IV catheter system according to claim 1, wherein a periphery of the base plate is provided with at least one resilient tongue, which in turn cooperates with the catheter hub body.

12. The IV catheter system according to claim 11, wherein the at least one resilient tongue is provided with a laterally extending protuberance.

13. The IV catheter system according to claim 1, wherein a periphery of the base plate includes 3 to 5 resilient tongues.

14. The IV catheter system according to claim 13, wherein the 3 to 5 resilient tongues are evenly distributed on and along the periphery of the base plate.

15. The IV catheter system according to claim 1, wherein the needle shield is a monolithic plastic body.

16. A catheter hub for an IV catheter system, said catheter hub comprising:
a tubular catheter attached at a proximal end to a catheter hub body;
a catheter hub cavity in fluid communication with a lumen of the tubular catheter;
a tube in fluid communication with the catheter hub cavity, said tube extending laterally from the catheter hub body;
a septum, proximal of the catheter hub cavity;
an end cavity, proximal of the septum;
a needle hub with a needle having a bulge; and
a needle shield with at least one resilient arm extending distally from a base plate having a through hole,
wherein the needle shield is arranged to be entirely housed in the end cavity in a retained manner through direct interaction between the needle shield and an inner wall of the catheter hub body in said end cavity, and onto the needle, such that the at least one arm rests upon and is spring loaded by the needle, and the needle is slidingly arranged within the through hole of the base plate, in an assembled state, and
wherein the bulge interacts with the base plate when the needle hub is withdrawn from the catheter hub to release the needle shield from the catheter hub and with the at least one arm covering a tip of the needle while the septum provides a seal, thereby forming a closed system in a released state.

17. The catheter hub according to claim 16, wherein the catheter hub comprises a tube connector extending laterally from the catheter hub body, and the tube in turn is attached to the tube connector.

18. The catheter hub according to claim 16, wherein a proximal end of the end cavity is provided with a ridge.

19. The catheter hub according to claim 16, wherein the catheter hub body is manufactured in polycarbonate or a copolymer of polycarbonate and polyester.

20. The catheter hub according to claim 16, wherein the septum is made of silicone or rubber.

* * * * *